United States Patent [19]
Vogelstein et al.

[11] Patent Number: 5,843,757
[45] Date of Patent: Dec. 1, 1998

[54] HUMAN JTV1 GENE OVERLAPS PMS2 GENE

[75] Inventors: Bert Vogelstein, Baltimore; Kenneth W. Kinzler, BelAir; Nicholas C. Nicolaides, Baltimore, all of Md.

[73] Assignee: The Johns Hopkins University, Baltimore, Md.

[21] Appl. No.: 518,862

[22] Filed: Aug. 24, 1995

[51] Int. Cl.⁶ ..................................................... C12N 1/21
[52] U.S. Cl. ..................... 435/252.3; 435/320.1; 435/254.11; 435/254.2; 536/23.1; 536/24.3; 536/24.31
[58] Field of Search .................. 536/23.1, 24.3, 536/24.31; 435/320.1, 240.2, 252.3, 254.11, 240.4, 254.2

[56] References Cited

PUBLICATIONS

Nicolaides et al., "Analysis of the 5' Region of PMS2 Reveals Heterogeneous Transcripts and a Novel Overlapping Gene", *Genomics* 29:329–334 (1995).
Hillier et al., "The WashU–Merck EST Project", EMBL Database Entry HS321180, Accession No. R84321 (1992).
Hillier et al., "The WashU–Merck EST Project", EMBL Database Entry HS461263, Accession No. N26461.
Nicolaides et al. (1994) Mutations of two PMS homologues in hereditary nonpolyposis colon cancer. Nature vol. 371, pp. 75–80.

*Primary Examiner*—Charles L. Patterson, Jr.
*Assistant Examiner*—Enrique D. Longton
*Attorney, Agent, or Firm*—Banner & Witcoff, Ltd.

[57] ABSTRACT

The hPMS2 gene encodes a protein which is involved in DNA mismatch repair and is mutated in a subset of patients with hereditary nonpolyposis colon cancer (HNPCC). The previously published hPMS2 cDNA sequence lacks an upstream in-frame stop codon preceding the presumptive initiating methionine. To further evaluate the 5' terminus of the hPMS2 coding region, we isolated additional cDNA clones, RT-PCR products, and the corresponding 5' genomic segment of the hPMS2 locus. The hPMS2 gene transcripts were found to have heterogeneous but collinear 5' termini, one of which contained an in-frame termination codon preceding the initiating methionine. In addition, a novel gene encoding a 34.5 kDa polypeptide was found to transcriptionally initiate within hPMS2 from the opposite strand.

6 Claims, 7 Drawing Sheets

FIG. 1

```
                                                                              -322
        TTA CCT GGT ACA TCG GCA TGG CAG AAC CAA AGC AAA AGG GGG TAG CGC
                                                              *   R
      V   P   K   A   N   A   Q   K   P   S   E   V   T   E   T        -273
-321  GTG CCA AAG GCC AAC GCT CAG AAA CCG TCA GAG GTC ACG GAG ACC
      G   H   L   P   S   D   P   A   G   V   R   E   N   A   V        -224
-272  GGC CAC CTC CCT TCT GAC CCT GCT GCG GTT CGG GAA AAC GCA GTC
      R   C   A   L   I   G   P   G   S   L   T   S   R   R   P        -175
-223  CGG TGT GCT CTG ATT GGC CCA GGC TCT TTG ACG TCA CGA AGT CGA CCT
      L   T   E   P   I   G   E   K   R   R   E   Y   F   L   P        -126
-174  TTG ACA GAG CCA ATA GGC GAA AAG CGG AGA GAA GTA TTT TTG CCG
      P   R   P   E   R   V   E   H   N   V   E   S   Q   W   E        -77
-125  CCC CGC CCG GAA AGG GTG CAC AAC GTC GAA AGC AGC CAA TGG GAG
      F   R   R   S   A   C   G   S   P   G   G   N   F   P   S        -28
-76   TTC AGG AGG CGG AGC TGT GGG AGC CCT GGA GGG AAC TTT CCC AGT
      P   R   G   G   S   V   A   S   M   E   R   A   E   S           +21
-27   CCC CGA GGC GGA TCG GGT GCA TCC GCA ATG GAG CGA GCT GAG AGC TCG
```

FIG. 2A

```
-113        CC GAA CGC CCG CAG CAG GGT CAG AAG GGA GGT GGC CGG TCT
   1                                                 M   P   M   Y
 -30        CGC GCT ACA CCC TTT TGC TTT GGT TCT GCC ATG CCG ATG TAC
  19         E   L   P   T   C   M   Y   R   L   P   N   V   H   G
 +55        GAG CTT CCC ACC TGC ATG TAC CGG CTC CCC AAC GTG CAC GGC
  47         E   S   N   L   S   L   Q   A   L   E   S   R   Q   D
+139        GAG TCT AAC CTG TCT CTG CAA GCT CTT GAG TCC CGC CAA GAT
  75         G   L   S   K   M   I   Q   T   P   D   A   D   L   D
+223        GGC CTC TCC AAG ATG ATT CAA ACA CCA GAT GCA GAC TTG GAT
 103         T   N   A   L   D   L   N   S   V   L   G   K   D   Y
+307        ACC AAT GCG CTG GAC TTG AAT TCA GTG CTT GGG AAG GAT TAC
 131         P   P   L   S   L   L   V   L   H   R   L   L   C   E
+391        CCT CCC CTC TCC CTG CTT GTG CTG CAC AGG CTG CTC TGT GAG
 159         K   S   V   P   E   N   L   L   K   C   F   G   E   Q
+475        AAG AGC GTG CCT GAA AAC CTT CTC AAG TGC TTT GGA GAA CAG
 187         L   I   W   K   N   V   P   K   T   Q   M   K   F   S
+559        TTA ATT TGG AAG AAT GTG CCG AAG ACG CAG ATG AAA TTC AGC
 215         R   F   L   F   S   L   F   G   Q   K   H   N   A   V
+643        CGT TTC TTG TTC TCT CTG TTT GGC CAG AAG CAT AAT GCT GTC
 243         Q   L   K   E   G   S   S   K   E   K   A   A   V   F
+727        CAG TTA AAA GAG GGA AGC AGT AAA GAA AAA GCC GCT GTT TTC
 271         G   N   E   L   T   V   A   D   V   V   L   W   S   V
+811        GGG AAT GAA CTC ACC GTA GCA GAC GTG GTG CTG TGG TCT GTA
 299         V   Q   R   W   M   R   S   C   E   N   L   A   P   F
+895        GTG CAG AGG TGG ATG AGG TCT TGT GAA AAC CTG GCT CCT TTT
+979        TTT TAA AGG GTT TAG ATT TTA AGA ATG GTG CTC TTT CAT GCC
+1063       ATT TAG GCC AGT TGT CAA GTG TCA ATA AAA GCG CAT CAT GTA
```

FIG. 2B

```
                                                              -31
CCG TCG TGA CCT CTG ACG GTT TCT GAG CGT TGG CCT TTG GCA
 Q   V   K   P   Y   H   G   G   A   P   L   R   V           18
CAG GTA AAG CCC TAT CAC GGG GGC GGC GCG CCT CTC CGT GTG       +54
 R   S   Y   G   P   A   P   G   A   G   H   V   Q   E        46
AGG AGC TAC GGC CCA GCG CCG GGC GCT GGC CAC GTG CAG GAA       +138
 D   I   L   K   R   L   Y   E   L   K   A   A   V   D        74
GAT ATT TTA AAA CGT CTG TAT GAG TTG AAA GCT GCA GTT GAT       +222
 V   T   N   I   I   Q   A   D   E   P   T   T   L   T        102
GTA ACC AAC ATA ATC CAA GCG GAT GAG CCC ACG ACT TTA ACC       +306
 G   A   L   K   D   I   V   I   N   A   N   P   A   S        130
GGG GCG CTG AAA GAC ATC GTG ATC AAC GCA AAC CCG GCC TCC       +390
 H   F   R   V   L   S   T   V   H   T   H   S   S   V        158
CAC TTG AGG GTC CTG TCC ACG GTG CAC ACG CAC TCC TCG GTC       +474
 N   K   K   Q   P   R   Q   D   Y   Q   L   G   F   T        186
AAT AAA AAA CAG CCC CGC CAA GAC TAT CAG CTG GGA TTC ACT       +558
 I   Q   T   M   C   P   I   E   G   E   G   N   I   A        214
ATC CAG ACG ATG TGC CCC ATC GAA GGC GAA GGG AAC ATT GCA       +642
 N   A   T   L   I   D   S   W   V   D   I   A   I   F        242
AAC GCA ACC CTT ATA GAT AGC TGG GTA GAT ATT GCG ATT TTT       +726
 R   S   M   N   S   A   L   G   K   S   P   W   L   A        270
CGC TCC ATG AAC TCT GCT CTT GGG AAG AGC CCT TGG CTC GCT       +810
 L   Q   Q   I   G   G   C   S   V   T   V   P   A   N        298
CTC CAG CAG ATC GGA GGC TGC AGT GTG ACA GTG CCA GCC AAT       +894
                                                              312
TAA CAC GGC CCT CAA GCT CCT TAA GTG AAT TGC CGT AAC TGA       +978
TAT TAT CAG TAA GGG GAC TTG TAT TAG AGT CAG AGT CTT TTT       +1063
ATT TAA AAA AAA AAA A                                         +1120
```

FIG. 4A

```
5'    -833  aca    ggccaatttctgtattttagtagagacgaggttttaccatgttggccaggcta
3'          tgt    tccggttaaagacataaaaatcatctctgctccaaaatggtacaaccggtccgat -773  gtc    aactcctgacctcaggtgatccgcccgcctcggcctcccaaagtgctgggatta
            cac    ttgaggactggagtccactaggcgggcggagccggagggtttcacgaccctaat -673  cac    tgagccacggcgcccggcctggataaatcttttaaaagataaaagtctgagtga
            gtc    actcggtgccgcgggccggacctatttagaaaattttctattttcagactcact -613  gtc    ggccggccggcacagatgccggggtggggccgtgaaccggttgggacgcgctcg
            cac    ccggccggccgtgtctacggccccaccccggcacttggccaaccctgcgcgagc -553  ctc    gcctggggggacccgggccagcagccggtcgccgcgcgtgcgcactgggcggggg
            gac    cggaccccctgggcccggtcgtcggccagcggcgcgcacgcgtgacccgccccc -493  gcc    gcgctcctacCTGCACGTGGCCAGGCCCGGCGCTGGGCCGTAGCTCCTGCCGTGC
            cgg    cgcgaggatgGACGTGCACCGGTCCGGGCCGCGACCCGGCATCGAGGACGGCACG -433  ACG    GGGGAGCCGGTACATGCAGGTGGGAAGCTCCACACGGAGAGGCGCGCCGCCCCG
            TGC    ACCCCTCGGCCATGTACGTCCACCCTTCGAGGTGTGCCTCTCCGCGCGGCGGGGC
```

FIG. 4B

```
-373  TGATAGGGCTTTACCTGGTACATCGGCATGGCAGAACCAAAGCAAAAGGGGGTAGCGCGT
      ACTATCCCGAAATGGACCATGTAGCCGTACCGTCTTGGTTTCGTTTTCCCCCATCGCGCA

-313  GCCAAAGGCCAACGCTCAGAAACCGTCAGAGGTCACGACGGAGACCGGCCACCTCCCTTC
      CGGTTTCCGGTTGCGAGTCTTTGGCAGTCTCCAGTGCTGCCTCTGGCCGGTGGAGGGAAG
                                                  <   <  <
-253  TGACCCTGCTGCGGGCGTTCGGGAAAACGCAGTCCGGTGTGCTCTGATTGGCCCAGGCCC
      ACTGGGACGACGCCCGCAAGCCCTTTTGCGTCAGGCCACACGAGACTAACCGGGTCCGGG
                   <        <
-193  TTTGACGTCACGAAGTCGACCTTTGACAGAGCCAATAGGCGAAAAGGAGAGACGGGAAGT
      AAACTGCAGTGCTTCAGCTGGAAACTGTCTCGGTTATCCGCTTTTCCTCTCTGCCCTTCA

-133  ATTTTTGCCGCCCCGCCCGGAAAGGGTGGAGCACAACGTCGAAAGCAGCCAATGGGAGTT
      TAAAAACGGCGGGGCGGGCCTTTCCCACCTCGTGTTGCAGCTTTCGTCGGTTACCCTCAA
                                >                     >        >
 -73  CAGGAGGCGGAGCGCCTGTGGGAGCCCTGGAGGGAACTTTCCCAGTCCCCGAGGCGGATC
      GTCCTCCGCCTCGCGGACACCCTCGGGACCTCCCTTGAAAGGGTCAGGGGCTCCGCCTAG

-13  GGGTGTTGCATCCATGGAGCGAGCTGAGAGCTCGAGgtgagcggggctcgcagtcttccg
      CCCACAACGTAGGTACCTCGCTCGACTCTCGAGCTCcactcgccccgagcgtcagaaggc +48  gtgtccctctcgcgcgccctctttgagacccacggcattccaacctccctggaaatggg 3
      cacaggggagagcgcgcgggagaaactctgggtgccgtaaggttggagggacctttaccc 5
```

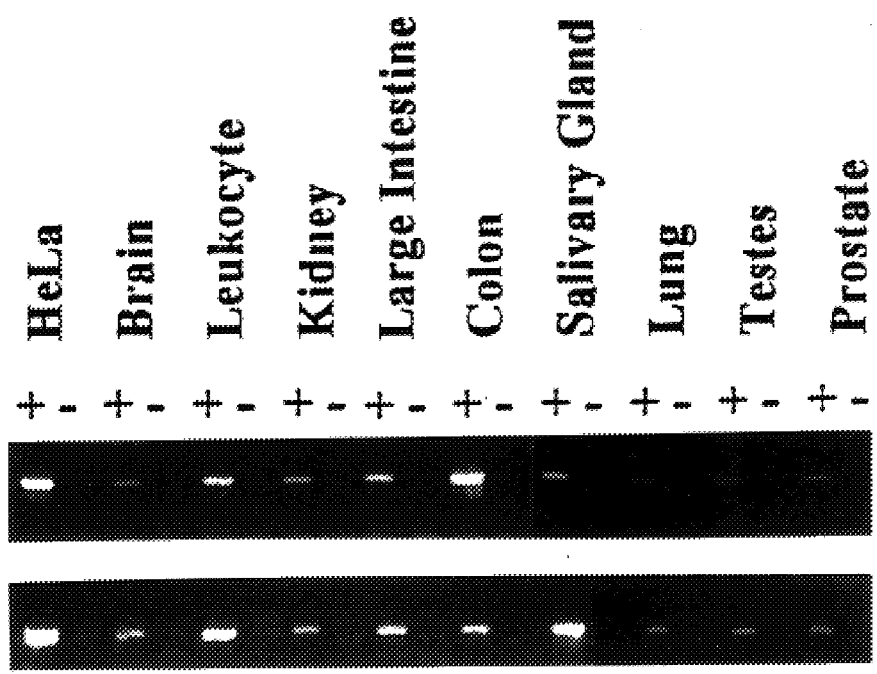

5,843,757

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 1233 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:1:

```
CCGAACGCCC  GCAGCAGGGT  CAGAAGGGAG  GTGGCCGGTC  TCCGTCGTGA  CCTCTGACGG      60

TTTCTGAGCG  TTGGCCTTTG  GCACGCGCTA  CACCCTTTTG  CTTTGGTTCT  GCCATGCCGA     120

TGTACCAGGT  AAAGCCCTAT  CACGGGGGCG  GCGCGCCTCT  CCGTGTGGAG  CTTCCCACCT     180

GCATGTACCG  GCTCCCCAAC  GTGCACGGCA  GGAGCTACGG  CCCAGCGCCG  GGCGCTGGCC     240

ACGTGCAGGA  AGAGTCTAAC  CTGTCTCTGC  AAGCTCTTGA  GTCCCGCCAA  GATGATATTT     300

TAAAACGTCT  GTATGAGTTG  AAAGCTGCAG  TTGATGGCCT  CTCCAAGATG  ATTCAAACAC     360

CAGATGCAGA  CTTGGATGTA  ACCAACATAA  TCCAAGCGGA  TGAGCCCACG  ACTTTAACCA     420

CCAATGCGCT  GGACTTGAAT  TCAGTGCTTG  GGAAGGATTA  CGGGGCGCTG  AAAGACATCG     480

TGATCAACGC  AAACCCGGCC  TCCCCTCCCC  TCTCCCTGCT  TGTGCTGCAC  AGGCTGCTCT     540

GTGAGCACTT  CAGGGTCCTG  TCCACGGTGC  ACACGCACTC  CTCGGTCAAG  AGCGTGCCTG     600

AAAACCTTCT  CAAGTGCTTT  GGAGAACAGA  ATAAAAAACA  GCCCCGCCAA  GACTATCAGC     660

TGGGATTCAC  TTTAATTTGG  AAGAATGTGC  CGAAGACGCA  GATGAAATTC  AGCATCCAGA     720
```

|   |   |   |   |   |   |   |   |   |   | |
|---|---|---|---|---|---|---|---|---|---|---|
| CGATGTGCCC | CATCGAAGGC | GAAGGGAACA | TTGCACGTTT | CTTGTTCTCT | CTGTTTGGCC | 780 |
| AGAAGCATAA | TGCTGTCAAC | GCAACCCTTA | TAGATAGCTG | GGTAGATATT | GCGATTTTTC | 840 |
| AGTTAAAAGA | GGGAAGCAGT | AAAGAAAAAG | CCGCTGTTTT | CCGCTCCATG | AACTCTGCTC | 900 |
| TTGGGAAGAG | CCCTTGGCTC | GCTGGGAATG | AACTCACCGT | AGCAGACGTG | GTGCTGTGGT | 960 |
| CTGTACTCCA | GCAGATCGGA | GGCTGCAGTG | TGACAGTGCC | AGCCAATGTG | CAGAGGTGGA | 1020 |
| TGAGGTCTTG | TGAAAACCTG | GCTCCTTTTT | AACACGGCCC | TCAAGCTCCT | TAAGTGAATT | 1080 |
| GCCGTAACTG | ATTTTAAAGG | GTTTAGATTT | TAAGAATGGT | GCTCTTTCAT | GCCTATTATC | 1140 |
| AGTAAGGGGA | CTTGTATTAG | AGTCAGAGTC | TTTTTATTTA | GGCCAGTTGT | CAAGTGTCAA | 1200 |
| TAAAAGCGCA | TCATGTAATT | TAAAAAAAAA | AAA |   |   | 1233 |

( 2 ) INFORMATION FOR SEQ ID NO:2:

( i ) SEQUENCE CHARACTERISTICS:
        ( A ) LENGTH: 312 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Met Tyr Gln Val Lys Pro Tyr His Gly Gly Gly Ala Pro Leu
 1               5                  10                  15

Arg Val Glu Leu Pro Thr Cys Met Tyr Arg Leu Pro Asn Val His Gly
            20                  25                  30

Arg Ser Tyr Gly Pro Ala Pro Gly Ala Gly His Val Gln Glu Glu Ser
        35                  40                  45

Asn Leu Ser Leu Gln Ala Leu Glu Ser Arg Gln Asp Asp Ile Leu Lys
    50                  55                  60

Arg Leu Tyr Glu Leu Lys Ala Ala Val Asp Gly Leu Ser Lys Met Ile
65                  70                  75                  80

Gln Thr Pro Asp Ala Asp Leu Asp Val Thr Asn Ile Ile Gln Ala Asp
                85                  90                  95

Glu Pro Thr Thr Leu Thr Thr Asn Ala Leu Asp Leu Asn Ser Val Leu
            100                 105                 110

Gly Lys Asp Tyr Gly Ala Leu Lys Asp Ile Val Ile Asn Ala Asn Pro
        115                 120                 125

Ala Ser Pro Pro Leu Ser Leu Leu Val Leu His Arg Leu Leu Cys Glu
    130                 135                 140

His Phe Arg Val Leu Ser Thr Val His Thr His Ser Ser Val Lys Ser
145                 150                 155                 160

Val Pro Glu Asn Leu Leu Lys Cys Phe Gly Glu Gln Asn Lys Lys Gln
                165                 170                 175

Pro Arg Gln Asp Tyr Gln Leu Gly Phe Thr Leu Ile Trp Lys Asn Val
            180                 185                 190

Pro Lys Thr Gln Met Lys Phe Ser Ile Gln Thr Met Cys Pro Ile Glu
        195                 200                 205

Gly Glu Gly Asn Ile Ala Arg Phe Leu Phe Ser Leu Phe Gly Gln Lys
    210                 215                 220

His Asn Ala Val Asn Ala Thr Leu Ile Asp Ser Trp Val Asp Ile Ala
225                 230                 235                 240

Ile Phe Gln Leu Lys Glu Gly Ser Ser Lys Glu Lys Ala Ala Val Phe
                245                 250                 255

Arg Ser Met Asn Ser Ala Leu Gly Lys Ser Pro Trp Leu Ala Gly Asn
            260                 265                 270
```

Glu Leu Thr Val Ala Asp Val Val Leu Trp Ser Val Leu Gln Gln Ile
        275                 280                 285

Gly Gly Cys Ser Val Thr Val Pro Ala Asn Val Gln Arg Trp Met Arg
        290                 295                 300

Ser Cys Glu Asn Leu Ala Pro Phe
305                 310

( 2 ) INFORMATION FOR SEQ ID NO:3:

( i ) SEQUENCE CHARACTERISTICS:
        ( A ) LENGTH: 384 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:3:

```
TTACCTGGTA  CATCGGCATG  GCAGAACCAA  AGCAAAAGGG  GGTAGCGCGT  GCCAAAGGCC      60
AACGCTCAGA  AACCGTCAGA  GGTCACGACG  GAGACCGGCC  ACCTCCCTTC  TGACCCTGCT     120
GCGGGCGTTC  GGGAAAACGC  AGTCCGGTGT  GCTCTGATTG  GCCCAGGCTC  TTTGACGTCA     180
CGAAGTCGAC  CTTTGACAGA  GCCAATAGGC  GAAAAGGAGA  GACGGGAAGT  ATTTTTGCCG     240
CCCCGCCCGG  AAAGGGTGGA  GCACAACGTC  GAAAGCAGCC  AATGGGAGTT  CAGGAGGCGG     300
AGCGCCTGTG  GGAGCCCTGG  AGGGAACTTT  CCCAGTCCCC  GAGGCGGATC  GGGTGTTGCA     360
TCCATGGAGC  GAGCTGAGAG  CTCG                                              384
```

( 2 ) INFORMATION FOR SEQ ID NO:4:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Arg Val Pro Lys Ala Asn Ala Gln Lys Pro Ser Glu Val Thr Thr Glu
1               5                   10                  15

Thr Gly His Leu Pro Ser Asp Pro Ala Ala Gly Val Arg Glu Asn Ala
                20                  25                  30

Val Arg Cys Ala Leu Ile Gly Pro Gly Ser Leu Thr Ser Arg Ser Arg
        35                  40                  45

Pro Leu Thr Glu Pro Ile Gly Glu Lys Glu Arg Arg Glu Val Phe Leu
        50                  55                  60

Pro Pro Arg Pro Glu Arg Val Glu His Asn Val Glu Ser Ser Gln Trp
65                  70                  75                  80

Glu Phe Arg Arg Arg Ser Ala Cys Gly Ser Pro Gly Gly Asn Phe Pro
                85                  90                  95

Ser Pro Arg Gly Gly Ser Gly Val Ala Ser Met Glu Arg Ala Glu Ser
                100                 105                 110

Ser ( 2 ) INFORMATION FOR SEQ ID NO:5:

( i ) SEQUENCE CHARACTERISTICS:
    ( A ) LENGTH: 900 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Homo sapiens ( x i ) SEQUENCE DESCRIPTION: SEQ ID NO:5:

```
ACACCCGGCC AATTTCTGTA TTTTTAGTAG AGACGAGGTT TTACCATGTT GGCCAGGCTA    60
GTCTCGAACT CCTGACCTCA GGTGATCCGC CCGCCTCGGC CTCCCAAAGT GCTGGGATTA   120
CAGGCGTGAG CCACGGCGCC CGGCCTGGAT AAATCTTTTA AAAGATAAAA GTCTGAGTGA   180
GTCCCTGGCC GGCCGGCACA GATGCCGGGG TGGGGCCGTG AACCGGTTGG GACGCGCTCG   240
CTCCGGCCTG GGGGGACCCG GGCCAGCAGC CGGTCGCCGC GCGTGCGCAC TGGGCGGGGG   300
GCCCCGCGCT CCTACCTGCA CGTGGCCAGG CCCGGCGCTG GGCCGTAGCT CCTGCCGTGC   360
ACGTTGGGGA GCCGGTACAT GCAGGTGGGA AGCTCCACAC GGAGAGGCGC GCCGCCCCG    420
TGATAGGGCT TTACCTGGTA CATCGGCATG GCAGAACCAA AGCAAAGGG GGTAGCGCGT    480
GCCAAAGGCC AACGCTCAGA AACCGTCAGA GGTCACGACG GAGACCGGCC ACCTCCCTTC   540
TGACCCTGCT GCGGGCGTTC GGGAAAACGC AGTCCGGTGT GCTCTGATTG GCCCAGGCCC   600
TTTGACGTCA CGAAGTCGAC CTTTGACAGA GCCAATAGGC GAAAAGGAGA GACGGGAAGT   660
ATTTTTGCCG CCCCGCCCGG AAAGGGTGGA GCACAACGTC GAAAGCAGCC AATGGGAGTT   720
CAGGAGGCGG AGCGCCTGTG GGAGCCCTGG AGGGAACTTT CCCAGTCCCC GAGGCGGATC   780
GGGTGTTGCA TCCATGGAGC GAGCTGAGAG CTCGAGGTGA GCGGGGCTCG CAGTCTTCCG   840
GTGTCCCCTC TCGCGCGCCC TCTTTGAGAC CCACGGCATT CCAACCTCCC TGGAAATGGG   900
```

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:6:

```
CGGGTGTTGC ATCCATGG                                                  18
```

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:7:

GGGTGGAGCA CAACGTCG 18

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:8:

GGTCACGACG GAGACCG 17

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:9:

TGCAGGTGGG AAGCTCCACA CGG 23

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:10:

TAGCTCCTGC CGTGCACG 18

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:11:

CGCTCCTACC TGCACGTG                                                                                  18

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:12:

TAGACTCAGT ACCACCTGC                                                                                 19

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:13:

TACAGAACCT GCTAAGGCC                                                                                 19

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:14:

TTTCTACTAA CTCCTTTACC G                                                                              21

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:15:

CAACCATGAG ACACATCGC 19

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:16:

AGGTTAGTGA AGACTCTGTC 20

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:17:

GTTCTGCCAT GCCGATG 17

( 2 ) INFORMATION FOR SEQ ID NO:18:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:18:

GGCCTTTGGC ACGCGCTAC 19

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:19:

ACCGGACTGC GTTTTCCCG ( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:20:

TCTCAGCTCG CTCCATGG ( 2 ) INFORMATION FOR SEQ ID NO:21:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:21:

GCAGAGACAG GTTAGACTC ( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:22:

GCTCCTTAAG TGAATTGCCG ( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:23:

TGACACTTGA CAACTGGCC                                                                                    19

HUMAN JTV1 GENE OVERLAPS PMS2 GENE

This invention was partially supported using N.I.H. grants CA35494 and CA62924. Therefore, the U.S. government retains certain rights in the invention.

BACKGROUND OF THE INVENTION

Hereditary Nonpolyposis Colon Cancer (HNPCC) is an autosomal dominantly inherited disease characterized by an early onset of colorectal cancer (CRC) (Lynch et.al., 1993). Virtually all tumors from HNPCC patients and a small fraction of non-hereditary CRC contain numerous alterations in microsatellite sequences throughout their genomes (Ionov et.al., 1993; Thibodeau et.al., 1993; Aaltonen et.al., 1993; Shibata, et.al., 1994). A hereditary defect in mismatch repair is likely to be responsible for both the microsatellite instability and tumor susceptibility in HNPCC patients (Parsons et.al., 1993; Umar, et.al., 1994). Four genes that participate in mismatch repair (hMSH2, hMLH1, hPMS1, and hPMS2) have been discovered and shown to be mutated in the germ-line of HNPCC patients (Fishel, et.al., 1993; Leach et.al., 1993; Palombo, et.al., 1994; Bronner et.al., 1994; Papadopoulos et.al., 1994; Nicolaides et.al., 1994).

Mismatch repair is initiated with the binding of MutS-related proteins to mismatched basepairs, and continues with the binding of mutL-related proteins to the mutS-DNA complex (reviewed in Modrich, 1995). Other components are then recruited to excise the DNA strand containing the mismatch and replace it with the correct nucleotides. Human mutL-related proteins involved in this pathway have recently been purified to homogeneity and shown to complement the mismatch repair activity of a human tumor cell line which is deficient in mismatch repair (Li and Modrich, 1994). The complementing activity is present in a heteroduplex that is comprised of a 85 and a 110 kDa protein. Sequence analysis of proteolytic peptides from the 85 kDa protein revealed it to be the product of hMLH1, and this protein's molecular weight agreed with that predicted from the cDNA sequence (Bronner et.al., 1994; Papadopoulos et.al., 1994). The sequence of the peptide generated from the 110 kDa component showed it to be similar to the hPMS2 mutL-homolog; however, the predicted molecular weight of hPMS2 is only 95 kDa (Nicolaides, et.al., 1994). Since the previously isolated hPMS2 cDNA clones lacked an in-frame termination codon upstream of the presumptive initiating methionine, it was possible that the open reading frame extended further upstream. Thus there is a need in the art for further knowledge of the genetic structures of and adjacent to the known hPMS2 gene.

SUMMARY OF THE INVENTION

It is an object of the invention to provide a novel, isolated, human gene on chromosome 7.

It is an object of the invention to provide vectors and host cells for making a novel human gene product.

It is another object of the invention to provide compositions of matter containing the human gene product.

These and other objects are provided by one or more of the embodiments described below. In one embodiment of the invention, a segment of a cDNA is provided. The cDNA consists of the sequence of nucleotides shown in SEQ. ID NO:1 and in FIGS. 2A and 2B.

According to another embodiment of the invention, a vector comprising the segment of cDNA which consists of the sequence of nucleotides shown in SEQ ID NO:1 and in FIGS. 2A and 2B is provided, as well as host cells comprising the vector.

According to still another embodiment of the invention, a composition is provided. The composition consists essentially of a protein consisting of the amino acid sequence shown in SEQ. ID NO: 2 and in FIGS. 2A and 2B.

In yet another embodiment of the invention a composition of protein JTV1 as shown in SEQ ID NO: 2 and FIG. 2 is provided. The composition is free of other human proteins.

In another embodiment of the invention a segment of cDNA (nucleotides 114 to 1049 of SEQ ID NO:1) is provided which segment encodes the amino acid sequence of JTV1 protein (SEQ ID NO: 2) shown in FIGS. 2A and 2B.

cDNA probes are also provided by the present invention. The CDNA portion of said probes consists of between 15 and 1176 contiguous nucleotides of the sequence shown in SEQ ID NO: 1.

BRIEF DESCRIPTION OF THE DRAWINGS

FIG. 1 shows the sequence of the 5' region of hPMS2 and predicted coding region SEQ ID NO:3 and SEQ ID NO:4. The arrow indicates the 5' end of the previously published cDNA clone. The presumptive initiating methionine is underlined.

FIGS. 2A and 2B show SEQ ID NO:1 and SEQ ID NO:2 shows the sequence of JTV1. The sequence has been deposited in Genbank, accession number U24169. The presumptive initiating methionine is underlined.

FIGS. 4A and 4B demonstrates the mapping of transcriptional start sites of hPMS2 and JTV1. Sequence of the genomic region containing the 5' ends of the two genes is shown SEQ ID NO: 5. The sequence is numbered in respect to codon 1 of hPMS2. Lower case letters denote intronic sequence of JTV1 (from nt−479 to −833) and hPMS2 (from +24 to +108). Arrows indicate the 5' ends of hPMS2 (sense strand) and of JTV1 (antisense strand) cDNA clones. The underlined ATG codons indicate the predicted initiating methionines for hPMS2 (at nt+1 on the sense strand) and JTV1 (at nt −345 on the antisense strand). The sequence has been deposited in Genbank, accession number U24168 and is shown in SEQ ID NO:5.

FIGS. 5A and 5B show the expression of hPMS2 and JTV1. RNA from various tissues was incubated with reverse transcriptase (RT+) or in control reactions without reverse transcriptase (RT-). The cDNA was used as template for PCR with primers specific for hPMS2 (A) and JTV1 (). RT-PCR products were separated by polyacrylamide gel electrophoresis.

DETAILED DESCRIPTION OF THE PREFERRED EMBODIMENTS

Figure 3:
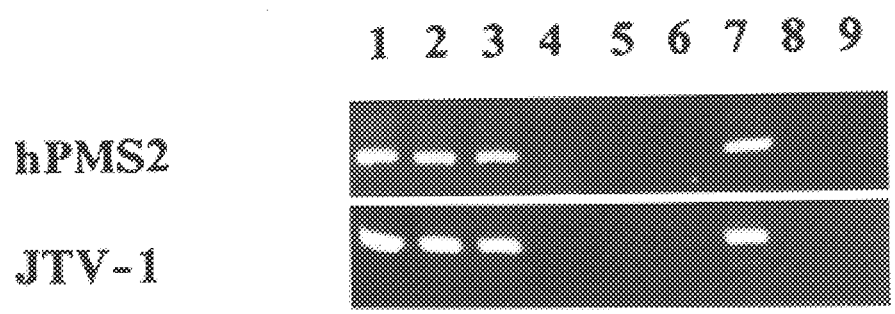
FIG. 3 demonstrates the genomic localization of JTV1. The genomic localization of hPMS2 and JTV1 were confirmed by screening somatic-cell hybrids containing various regions of human chromosome 7. Lane 1, GM10791 contains entire chromosome 7 in a chinese hamster ovary (CHO) background; lane 2, NA11440 contains 7pter>7p22 in a CHO background; lane 3, Ru-Rag4-13 contains 7cen-7pter in a murine background; lane 4, 4AF1/106/K015 contains 7center in a murine background; lane 5, GM05184.17 contains 7q21.2-qter in a CHO background; lane 6, 2068Rag22-2 contains 7q22-qter in a murine background; lane 7, human genomic DNA; lane 8, mouse genomic DNA; lane 9, CHO genomic DNA.

To investigate the upstream region from hPMS2, we isolated additional cDNA clones, analyzed the 5' end of hPMS2 transcripts with PCR-based techniques, and cloned the corresponding genomic segments. In addition to clarifying the transcript, we serendipitously discovered a previously undescribed gene overlapping hPMS2. That gene is termed herein JTV1. The sequences of the JTV1 cDNA and protein are shown in SEQ ID NOS: 1 and 2, respectively.

A segment of cDNA according to the present invention refers to a contiguous stretch of deoxyribonucleotides which have a sequence as obtained upon reverse transcriptase of an RNA transcript. Such segments do not contain introns. The segment may be an isolated molecule or it can be covalently joined to other nucleic acid sequences. The segment may, for example, be replicated as part of a vector, such as a plasmid, virus, or minichromosome. The vector may be replicated within a host cell, such as a cell transformed by a recombinant DNA molecule. The host cell may be used to produce JTV1 protein. It can also be used to study regulation of expression of JTV1 sequences, for example by subjecting the host cell to various agents which may or may not affect the expression. Although the DNA sequence is discussed with particularity herein, it is well within the skill of the art to make small mutations, such as single nucleic acid substitutions of one of the other three nucleic acid bases, at any of the positions of the sequence. In addition, it is well within the art to make single base deletions or single base insertions, to study the effect upon protein structure and function.

If JTV1 is produced in a recombinant host cell which is not human, a composition of JTV1 protein will be produced which is free of other human proteins. If JTV1 protein is isolated from naturally producing cells, or from human host cells, then the protein can be purified, for example, using antibodies which are raised against an immunogen comprising JTV1 amino acid sequence. Any other means of purification known in the art can be used, as is desired.

DNA molecules can be made having different nucleotide sequences from that disclosed in SEQ ID NO: 1, but which still encode the JTV1 protein as disclosed in SEQ ID NO:2. Using the known coding relationships between codons and amino acids and the disclosed amino acid sequence, numerous other sequences can be readily designed and produced. Such DNA molecules are within the contemplation of the subject invention.

cDNA probes can be used for hybridization studies. Typically they are labeled with a detectable marker, such as a radiolabel or a fluorescent moiety, although they need not be. The cDNA probes of the subject invention consist of at least 15 contiguous nucleotides of the sequence shown in SEQ ID NO: 1. If greater specificity is desired, larger molecules of 18, 20, 25, or 30 nucleotides can be used, up to a maximum of the entire sequence of 1176 nucleotides.

JTV1 cDNAs can be used as probes to detect deletions in chromosome 7. Due to the overlapping promoter regions, large deletions of JTV1 would also be expected to affect PMS2 expression, leading to Hereditary Non-Polyposis Colorectal Cancer (HNPCC). JTV1cDNA can be used in chromosome mapping. It can also be used to assay activity or competence of the PMS2 promoter region. The presence of JTV1 transcripts or JTV1 protein suggests that the PMS2 promoter is intact. If the PMS2 promoter is intact and PMS2 products are absent, a structural defect in the coding region is indicated.

JTV1 sequences can be used to guide homologous recombination at the PMS2 locus. For example, where a PMS2 mutation is present and therapeutic replacement with a wild-type gene is desired, PMS2 sequences can be used to provide an adjacent region of homology. Similarly, it may be desirable to target other genes to the region adjacent to PMS2. JTV1 sequences can be used to flank such other genes, providing one or more regions of homology. If insertion of other genes is desired between the JTV1 and the PMS2 sequences, again, this can be accomplished using the identified sequences as homology units for homologous recombination.

EXAMPLES

Example 1

Isolation and sequence analysis of the 5' end of hPMS2.

Purified DNA from P1 clone 53, previously determined to contain the hPMS2 gene (Nicolaides, et.al., 1994), was digested with EcoRI and subcloned into the pBluescript vector (Stratagene). Clones containing the 5' region of hPMS2 were identified by hybridization with primer A (SEQ ID NO: 6) (Table 1) directed to exon 1. Restriction analysis of several positive clones showed them to be identical. The sequence of the relevant region of hPMS2 was determined from both strands using $^{35}$S α-dATP and Sequenase (USB).

TABLE 1

Primers used for hPMS2.

| PRIMER NAME | STRAND | PRIMER SEQUENCE | POSITION* |
|---|---|---|---|
| A (SEQ ID NO: 6) | sense | 5'-cgggtgttgcatccatgg-3' | −14−+4 |
| B (SEQ ID NO: 7) | sense | 5'-gggtggagcacaacgtcg -3' | −110—93 |
| C (SEQ ID NO: 8) | sense | 5'-ggtcacgacggagaccg-3' | −283—267 |
| D (SEQ ID NO: 9) | sense | 5'-tgcaggtgggaagctccacacgg-3' | −414—392 |
| E (SEQ ID NO: 10) | sense | 5'-tagctcctgccgtgcacg-3' | −448—431 |
| F (SEQ ID NO: 11) | sense | 5'-cgctcctacctgcacgtg-3' | −487—470 |
| G (SEQ ID NO: 12) | antisense | 5'-tagactcagtaccacctgc-3' | +90−+107 |
| H (SEQ ID NO: 13) | sense | 5'-tacagaacctgctaaggcc-3' | +24−+42 |
| I (SEQ ID NO: 14) | antisense | 5'-tttctactaactccttaccg-3' | +116−+136 |
| J (SEQ ID NO: 15) | sense | 5'-caaccatgagacacatcgc-3' | +2545− |
| K (SEQ ID NO: 16) | antisense | 5'-aggttagtgaagactctgtc-3' | +2647−+2666 |

*Relative to the presumptive initiating methionine in FIG. 1.

Three clones were isolated, each containing an 8.5 kb EcoRI insert. Partial sequence analysis of one clone, pSMN, determined that it contained coding residues of hPMS2 as well as sequences upstream of the previously designated codon 1. The presumptive initiating codon reported previously has been designated as nucleotide 1 in FIG. 1. The sequence of hPMS2 was extended 833 bp upstream of nucleotide 1. This sequence revealed an in-frame stop codon 321 nts upstream of the published initiator methionine, with no intervening methionines (FIG. 1).

Example 2
Isolation of additional cDNA clones using hPMS2 probes.

Two cDNA libraries were screened with a probe containing nt +24 to +136 of hPMS2 generated by PCR using P1 clone 53 as template and the primers H and I (Table 1). A human small intestine random-primed cDNA library in λGT10(Clontech) and a HeLa oligo-dT primed cDNA library in λZAPII (Stratagene) were screened as described except hybridizations were carried out at 68° C. and filters were washed at 65° C. for 0.5 hrs (Kinzler and Vogelstein, 1989). Following plaque purification, the EcoRI inserts from the small intestine library were subcloned into pBluescript vector, while the HeLa cDNA inserts were rescued as phagemids following the manufacturer's protocol (Stratagene).

One clone was isolated from the random-primed small intestine library, and this contained nt−14 to nt+1668 of hPMS2. Two clones were isolated from the oligo-dT primed HeLa cDNA library. The clones began at nt−53 and ended at either nts+2722 or +2749. The HeLa cDNA library was also screened with a 430 bp probe from the 5' genomic region of hPMS2, containing nt−414 to +16, generated by PCR from P1 clone 53 using primers D (Table 1) and O (Table 2). The same two clones were identified, as expected. However, twelve other overlapping clones were found and appeared to represent a different transcript, named JTV1 (FIGS. 2A and 2B). These twelve cDNAs were approximately 1.2 kb in length and were sequenced in their entirety. All twelve ended with a polyA tract (assumed to be the 3' end) and were identical for 1.2 kb upstream. The 5' ends were located within 38 bp of each other. Comparison with hPMS2 indicated that JTV1 was transcribed from the opposite strand.

TABLE 2

Primers used for JTV-1 cDNA amplification.

| PRIMER NAME | STRAND | PRIMER SEQUENCE | POSITION* |
| --- | --- | --- | --- |
| L (SEQ ID NO: 17) | sense | 5'-gttctgccatgccgatg-3' | −8−+9 |
| M (SEQ ID NO: 18) | sense | 5'-ggcctttggcacgcgctac-3' | −23—41 |
| N (SEQ ID NO: 19) | sense | 5-accggactgcgttttcccg-3' | −111—129 |
| O (SEQ ID NO: 20) | sense | 5'-tctcagctcgctccatgg-3' | −343—360 |
| P (SEQ ID NO: 21) | antisense | 5'-gcagagacaggttagactc-3' | +139−+157 |
| Q (SEQ ID NO: 22) | sense | 5'-gctccttaagtgaattgccg-3' | +952−+971 |
| R (SEQ ID NO: 23) | antisense | 5'-tgacacttgacaactggcc-3' | +1068−+1086 |

*Relative to the presumptive initiating methionine in FIGS. 2A and 2B

Example 3
JTV1.

The length of one clone representative of JTV1 (pM23NNFL) was 1233 bp and encoded an open reading frame (ORF) of 936 bp (FIGS. 2A and 2B). The first methionine within this ORF was designated codon 1 (FIGS. 2A and 2B) and was preceded by an in-frame termination codon 66 bp upstream. This methionine had a reasonable match to the Kozak translation initiation consensus (Kozak, 1986). The 3' end contained a polyadenylation signal (AAUAAA) starting at nucleotide 1086 followed by a polyA tail. The transcript was predicted to encode a polypeptide of 312 amino acids, with a molecular weight of 34.5 kda. Searches of nucleotide and peptide sequence databases showed that this was a novel gene, with limited homology to the glutathione S-transferase gene family.

Example 4
Chromosomal Mapping of JTV1.

The hPMS2 locus was previously mapped to chromosome 7p22 by FISH using P1 clone 53 (Nicolaides et.al., 1994). Because multiple hPMS2-related genes are located on the long arm of chromosome 7 and have conserved 5' regions (personal observation, Hori et.al., 1994), we confirmed the genomic localization of JTV1 by PCR analysis of rodent-human somatic cell hybrid DNAs containing various regions of chromosome 7 (Scherer et.al., 1993; Powers et.al., 1993). PCR primers were chosen from the 3' untranslated region of hPMS2 and JTV1 and shown to amplify genomic DNA. hPMS2 primers J and K yielded a 121 bp product and JTV1 primers Q and R yielded a 134 bp product. PCR products for both genes were formed in those DNAs containing the 7p22 region: lines GM10791 (containing the entire human chromosome 7), NA11440 (Coriell Institute) (7p22>7pter) and Ru-Rag4-13 (7cen-7pter) (FIG. 3, lanes 1, 2, and 3). No products were observed in lines 4AFl/106/K015 (7cen-qter), GM05184.17 (7q21.2-qter), or 2068Rag22-2 (7q22-qter) (FIG. 3, lanes 4, 5, and 6).

Example 5
Analysis of the 5' Termini of hPMS2 and JTV1.

The 5' termini of hPMS2 transcripts were studied by standard cDNA cloning, RACE, and RT-PCR analyses. RNA was purified from tissues and cells using a guanidine isothiocyanate based method (Chomczynski and Sacchi, 1987). Reverse transcriptase-polymerase chain reaction (RT-PCR) was performed using randomly primed cDNA as template as described (Leach, et.al., 1993). RT-PCR of the 5' end of hPMS2 was performed using a common antisense primer (I) and the sense primers (A-F) described in Table 1. RT-PCR mapping of the 5' end of JTV1 was done using a common antisense primer P and the sense primers L-O as described in Table 2. RACE (rapid amplification of cDNA ends, Frohman, et.al., 1988) was performed on hPMS2 using sequential antisense primers I and G (Table 1) following the manufacturer's protocol (Clontech). RACE analysis of JTV1 was done using the antisense primer P (Table 2). Amplification products were cloned into a T-tailed vector (InVitrogen) and sequenced using SP6 and T7 primers. Amplifications were done at 95° C. for 30 sec, 56° C. for 1.5 min., and 70° C. for 1.5 min for 35 cycles. Reaction products were separated by electrophoresis in 6% nondenaturing polyacrylamide gels.

FIGS. 4A and 4B show the sequence of the genomic region containing the transcriptional initiation sites of both hPMS2 and JTV1, numbered as in FIG. 1 with respect to hPMS2. The 5' ends of hPMS2 cDNA clones are marked with arrowheads on the top strand. One clone began at nt−14, one at nt−24, and two at nt−53. RACE products were generated from adult brain, leukocyte, and placenta MRNA. Using an antisense primer corresponding to nt+116 to +136, multiple bands with approximately 160 to 191 bps were observed in addition to less intense bands of up to 550 bp. The sequence of four cloned RACE products demonstrated that, as expected, their 5' ends were located between nt -25 to -55. These data suggested that the majority of hPMS2 transcripts initiated between nt −13 to −55, with a minority extending further upstream. This was confirmed by RT-PCR analysis using mRNA from HeLa cells as template. Robust RT-PCR products were amplified with sense primers whose 5' ends were at nt−14, −110, −283, and −414, (primers A, B, C, and D; Table 1) and an antisense primer corresponding to nt +90 to +107 (G). No PCR products were observed using sense primers whose 5' ends were at nt −448 or −487 (primers E and F). To ensure that primers E and F were not defective, successful amplification of genomic DNA was performed using these primers and an antisense primer (O) corresponding to nt−2 to +16.

The 5' termini of JTV1 showed a heterogeneous pattern like that of hPMS2. The 5' ends of the 12 cDNA clones are indicated by arrowheads on the bottom strand in FIG. 4. They were located 73 to 113 nt 73 upstream of codon 1 of JTV1, which corresponded to nt−271 to −232 of hPMS2. RACE confirmed the cDNA results in that the majority of products generated using an antisense primer P corresponding to JTV1 nt+157 were 230 to 270 bp. RT-PCR analysis was performed with antisense primer P and several sense primers (L-O) listed in TABLE 2. PCR products were found with sense primers whose 5' ends were at −8, −23, and −111, (primers L,M, and N) but not with a sense primer O whose 5' end was at nt−360 with respect to JTV1, nt +1. The latter primer was not defective, as a genomic segment could be successfully amplified with it.

Transcripts of hPMS2 had heterogeneous but collinear 5' termini, containing 11 to 415 nt of presumably untranslated sequence. The transcripts contained an in-frame stop codon upstream of the presumptive initiating methionines (FIG. 1), making the originally described methionine the most likely translation initiator. Because no other upstream coding regions of hPMS2 appeared to exist, the size discrepancy between that predicted from the hPMS2 sequence and the 110 kDa hPMS2 protein identified by Li and Modrich is likely due to post-transcriptional modifications or alternative internal exons.

Our results revealed that hPMS2 overlaps with a novel gene, JTV1, transcribed from the opposite strand (FIGS. 4A and 4B). This organization is similar to that of H)MDUG, a mutS-homolog found on human chromosome 5, and the dihydrofolate reductase (DBFR) gene (Fujii and Shimada, 1989). Both hPMS2-JTV1 and HUMDUG-DHFR lie in a head to head arrangement, both genes are ubiquitously expressed, and both have multiple 5' termini. It has been hypothesized that DHFR and HUMDUG may be regulated via a bidirectional promoter, because a minor subset of the transcripts from the two genes overlap. The major transcripts of HUMDUG and DHFR, however, do not overlap, as is true for hPMS2 and JTV1. It will be of interest to determine whether other mismatch repair genes are arranged in a head to head fashion with a contiguous gene and if JTV1 is involved in DNA replication or repair.

Example 6
Expression of hPMS2 and JTV1.

The expression of hPMS2 and JTV1 was analyzed in a variety of mRNA samples prepared from human tissues. RT-PCR was performed on cDNA templates derived from adult brain, leukocytes, kidney, large intestine, colon, salivary gland, lung, testes and prostate using primers J and K for hPMS2 and primers Q and R for JTV1 (Tables 1 and 2). Both genes were expressed in all tissues tested (FIG. 5).

REFERENCES

Aaltonen, L. A., Peltomaki, P., Leach, F. S., Sistonen, P., Pylkkanen, L., Mecklin, J.-P., Jarvinen, H., Powell, S. M., Jen, J., Hamilton, S. R., Petersen, G.M., Kinzler, K. W., Vogelstein, B., and de la Chapelle, A. (1993). Clues to the pathogenesis of familial colorectal cancer. *Science* 260:812–816.

Chomczynski, P., and Sacchi, N. (1987). Single step method of RNA isolation by acidic guanidinium-isothiocyanate phenol-chloroform extraction. *Anal. Biochem.* 162:6–13.

Bronner, C. E., Baker, S. M., Morrison, P. T., Warren, G., Smith, L. G., Lescoe, M. K., Kane, M., Earabino, C., Lipford, J., Lindblom, A., Tannergard, P., Bollag, R. J., Godwin, A. R., Ward, D.C., Nordenskold, M., Pishel, R., Kolodner, R., and Liskay, R. M. (1994). Mutation in the DNA mismatch repair gene homologue hMLH1 is associated with hereditary non-polyposis colon cancer. *Nature* 368:258–261.

Fishel, R., Lescoe, M., Rao, M. R. S., Copeland, N. G., Jenkins, N. A., Garber, J., Kane, M., and Kolodner, R. (1993). The human mutator gene homolog MSH2 and its association with hereditary nonpolyposis colon cancer. *Cell* 75:1027–1038.

Frohman, M. A., Dush, M. K., and Martin, G. R. (1988). Rapid production of full-length cDNAs from rare transcripts: amplification using a single gene-specific oligonucleotide primer. *Proc. Natl. Acad. Sci. USA* 85:8998–9002.

Fujii, H., and Shimada, T. (1989). Isolation and characterization of cDNA clones derived from the divergently transcribed gene in the region upstream from the human dihydrofolate reductase gene. *J. Biol. Chem.* 264:10057–10064.

Hori, A., Han, H.-J., Sasaki, S., Shimada, M., and Nakamura, Y. (1994). Cloning, characterization and chromosomal assignment of the human genes homologous to yeast PMS1, a member of mismatch repair genes. *Biochem. Biophys. Res. Comm.* 204:1257–1264.

Ionov, Y., Peinado, M. A., Malkbosyan, S., Shibata, D., and Perucho, M. (1993). Ubiquitous somatic mutations in simple repeated sequences reveal a new mechanism for colonic carcinogenesis. *Nature* 260:558–561.

Kinzler, K. W., and Vogelstein, B. (1989). Whole genome PCR: application to the identification of sequences bound by gene regulatory proteins. *Nuc. Acid. Res.* 17:3645–3653.

Kozak, M. (1986). Point mutations define a sequence flanking the AUG initiator codon that modulates translation by eucaryotic ribosomes. *Cell* 44:283–292.

Leach, F. S., Nicolaides, N.C., Papadopoulos, N., Liu, B., Jen, J., Parsons, R., Peltomaki, P., Sistonen, P., Aaltonen, L. A., Nystrom-Lahti, M., Guan, X.-Y., Zhang, J., Meltzer, P.S., Yu, J.-W., Kao, F.-T., Chen, D. J., Cerosaletti, K. M., Fournier, R. E. K., Todd, S., Lewis, T., Leach, R. J., Naylor, S. L., Weissenbach, J., Mecklin, J.-P., Jarvinen, J. A., Petersen, G.M., Hamilton, S. R., Green, J., Jass, J., Watson, P., Lynch, H. T., Trent, J. M., de la Chapelle, A., Kinzler, K. W., and Vogelstein, B. (1993). Mutations of a mutS homolog in hereditary nonpolyposis colorectal cancer. *Cell* 75:1215–1225.

Li, G.-M., and Modrich, P. (1994). Restoration of mismatch repair to nuclear extracts of H6 colorectal tumor cells by a heterodimer of human mutL homologs. *Proc. Natl. Acad. Sci. USA* 92:1950–1954.

Lynch, H. T., Smyrk, T. C., Watson, P., Lanspa, S. J., Lynch, J. F., Cavalieri, R. J., and Boland, C. R. (1993). Genetics, natural history, tumor spectrum, and pathology of hereditary nonpolyposis colorectal cancer: An updated review. *Gastroenterology* 104:1535–1549.

Modrich, P. (1995). Mismatch repair, genetic stability, and cancer. *Science* 266:1959–1960.

Nicolaides, N. C., Papadopoulos, N., Liu, B., Wei, Y.-F., Carter, K. C., Ruben, S. M., Rosen, C. A., Haseltine, W. A., Fleischmann, R. D., Fraser, C. M., Adams, M. D., Venter, J. C., Dunlop, M. G., Hamiltom, S. R., Petersen, G. M., de la Chapelle, A., Vogelstein, B., and Kinzler, K. W. (1994). Mutations of two PMS homologues in hereditary nonpolyposis colon cancer. *Nature* 371:75–80.

Palombo, F., Hughes, M., Jiricny, J, Truong, O., and Hsuan, J. (1994). Mismatch repair and cancer. *Nature* 367:417–418.

Papadopoulos, N., Nicolaides, N.C., Wei, Y.-F., Ruben, S.M., Carter, K. C., Rosen, W. A., Haseltine, W. A., Fleischmann, R. D., Fraser, C. M., Adams, M. D., Venter, J. C., Hamilton, S. R., Petersen, G. M., Watson, P., Lynch, H. T., Peltomaki, P., Mecklin, J.-P., de la Chapelle, A., Kinzler, K. W., and Vogelstein, B. (1994). Mutation of a mutL homolog in hereditary colon cancer. *Science* 263:1625–1629.

Parsons, R., Li, G.-M., Longley, M. J., Fang, W.-H., Papadopoulos, N., Jen, J., de la Chapelle, A. Kinzler, K. W., Vogelstein, B., and Modrich, P. (1993). Hypermutability and mismatch repair deficiency in RER+ tumor cells. *Cell* 75: 1227–1236.

Powers, P. A., Scherer, S. W., Tsui, L.-C., Gregg, R. G., Hogan, K. (1994). Localization of the gene encoding the $\alpha_2/\delta$ subunit (CACNL2A) of the human skeletal muscle voltage-dependent $Ca^{2+}$ channel to chromosome 7q21–22 by somatic cell hybrid analysis. *Genomics* 19:192–193.

Scherer, S. W., Neufeld, E. J., Lievens, P. M. -J., Orkin, S. H., Kim, J., and Tsui, L. -C. (1993). Regional localization of the CCAAT displacement protein gene (CUTL1) to 7q22 by analysis of somatic cell hybrids. *Genomics* 15:695–696.

Shibata, D., Peinado, M. A., Ionov, Y., Malkhosyan, S., and Perucho, M. (1994). Genomic instability in repeated sequences is an early somatic event in colorectal tumourigenesis that persists after transformation. *Nature Genet.* 6:273–281.

Thibodeau, S. N., Bren, G., and Schaid, D. (1993). Microsatellite instability in cancer of the proximal colon. *Science* 260:816–819.

Umar, A., Boyer, J. C., Thomas, D. C., Nguyen, D. C., Risinger, J.I. Boyd, J., Ionov, Y., Perucho, M., and Kunkel, T. A. (1994). Defective mismatch repair in extracts of colorectal and endometrial cancer cell lines exhibiting microsatellite instability. *J. Biol. Chem.* 269:14367–14370.

We claim:

1. A segment of cDNA consisting of the nucleotide sequence shown in SEQ ID NO:1.

2. A vector comprising the segment of DNA of claim 1.

3. A host cell which comprises the vector of claim 2.

4. A segment of cDNA which encodes the amino acid sequence of JTV1 protein shown in SEQ ID NO:2.

5. A vector comprising the segment of DNA of claim 4.

6. A host cell which comprises the vector of claim 5.

* * * * *